United States Patent [19]

Haber et al.

[11] Patent Number: 4,950,250

[45] Date of Patent: Aug. 21, 1990

[54] COLLAPSIBLE NEEDLE COVER

[75] Inventors: Terry M. Haber, El Toro; John A. Lewis, Costa Mesa, both of Calif.

[73] Assignee: Habley Medical Technology Corporation, Laguna Hills, Calif.

[21] Appl. No.: 404,672

[22] Filed: Sep. 8, 1989

Related U.S. Application Data

[63] Continuation of Ser. No. 159,373, Feb. 23, 1988.

[51] Int. Cl.⁵ .............................................. A61M 5/32
[52] U.S. Cl. .................................. 604/192; 604/198; 604/263
[58] Field of Search .............................. 128/766–768; 604/110, 111, 162, 163, 192, 197, 198, 117, 263; 206/365, 366

[56] References Cited

U.S. PATENT DOCUMENTS

| | | | |
|---|---|---|---|
| 3,904,033 | 9/1978 | Haerr | 604/263 |
| 4,139,009 | 2/1979 | Alvarez | 604/198 |
| 4,725,267 | 2/1988 | Vaillancourt | 604/198 |
| 4,735,618 | 4/1988 | Hagen | 604/195 |
| 4,790,828 | 12/1988 | Dombrowski | 604/195 |
| 4,820,277 | 4/1989 | Norelli | 604/263 |

Primary Examiner—Randall L. Green
Assistant Examiner—K. M. Reichle
Attorney, Agent, or Firm—Morland C. Fischer

[57] ABSTRACT

A safety enhancing, relatively low-cost, needle cover which is integrally bonded to a disposable needle cannula of a hypodermic syringe and adapted to eliminate the handling and/or destruction of the needle after use. The needle cover comprises distally and proximally oriented pairs of needle cover segments which are hingedly interconnected and pivotable relative to one another. The needle cover is collapsible from an open, expanded configuration, with the cannula biased in an armed state for administering an injection of the fluid contents of the syringe, to a closed, generally planar configuration, with the cannula biased in a shielded state completely surrounded, shielded and isolated after use. By virtue of the present invention, the needle cannula can be safely discarded within its collapsible cover while avoiding an accidental needle strike and the spread of a contagious, and possible life threatening disease.

13 Claims, 2 Drawing Sheets

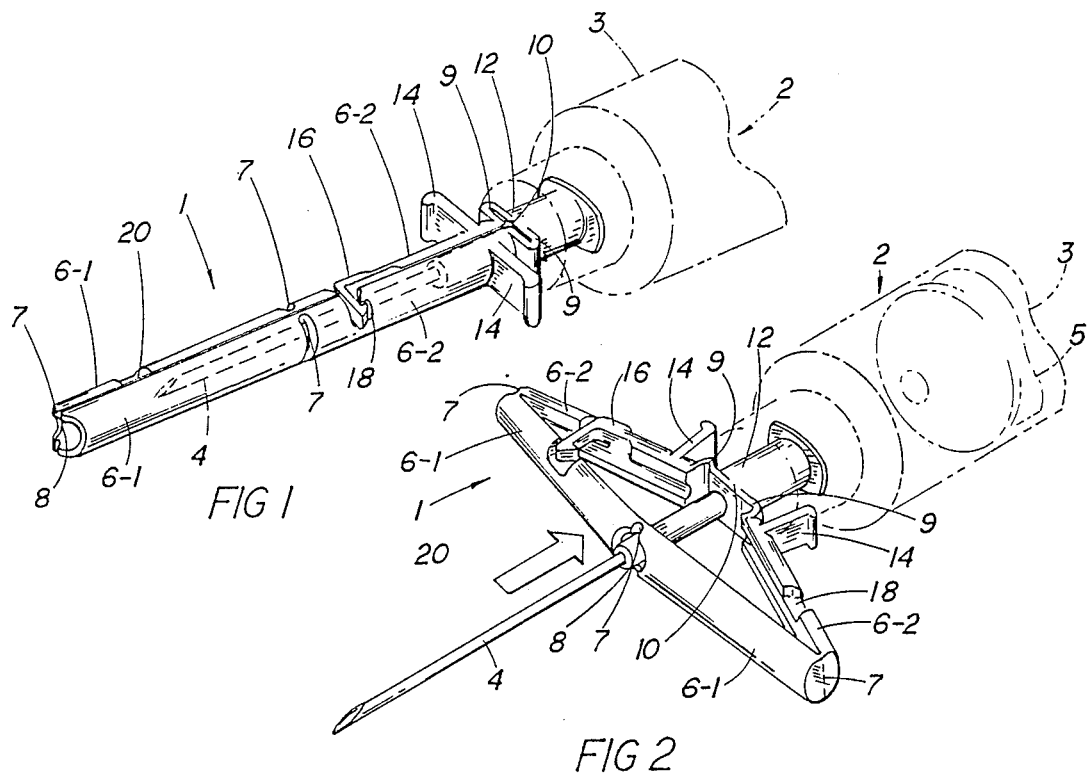
FIG 1
FIG 2
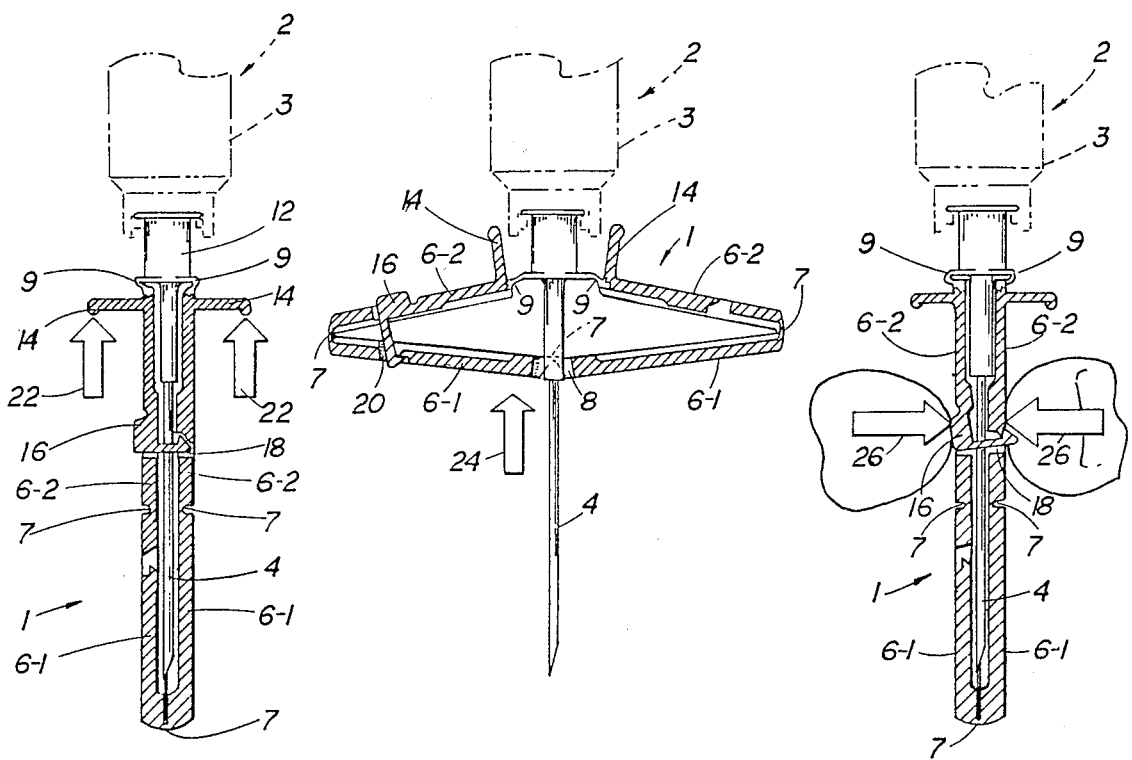
FIG 3
FIG 4
FIG 5

COLLAPSIBLE NEEDLE COVER

CROSS-REFERENCE TO RELATED PATENT APPLICATIONS

This patent application is a continuation of patent application Serial No. 159,373, filed Feb. 23, 1988.

BACKGROUND OF THE INVENTION

1. Field of the Invention

This invention relates to a safety enhancing and relatively low-cost needle cover which is integrally connected to a disposable needle cannula of a hypodermic syringe, wherein the cover is collapsible from an open, expanded configuration, at which the cannula is exposed for administering an injection, to a closed, generally planar configuration, at which the cannula is completely surrounded, shielded, and isolated after use.

2. Prior Art

Hypodermic syringes are used for a variety of purposes. By way of example, the syringe may be used to expulse fluid medication to a patient by way of a hypodermic needle cannula. However, the syringe may be used to treat a patient with a communicable disease. Prior to disposal of the syringe, the needle cannula thereof is sometimes broken to prevent reuse. Health care workers are especially susceptible to accidental and potentially infectious needle strikes due to the careless handling or breaking of the cannula and disposing of the syringe after use. The resulting mini-accidents caused by an inadvertent needle strike typically require a blood test for such diseases as AIDS and Hepatitus. The corresponding cost and inefficiency of testing health care workers who have received an inadvertent needle strike result in considerable waste, which may be particularly damaging to a health care facility which is striving for economy.

In our copending patent application filed concurrently herewith and entitled "COLLAPSIBLE BLOOD COLLECTOR", a safety enhancing, relatively low-cost, collapsible needle cover is described which is associated with a double-ended hypodermic needle cannula and a collapsible blood collection tube holder within which a blood sample may be automatically drawn from a patient. The present invention is directed to a collapsible needle cover which is associated with a hypodermic needle cannula and a syringe cylinder from which a fluid medication, or the like, may be expulsed to a patient.

SUMMARY OF THE INVENTION

In general terms, this invention relates to a safety enhancing, relatively low-cost, needle cover which is integrally bonded to and collapsible around a disposable, single use needle cannula. In a first embodiment of the invention, the combination cannula and collapsible needle cover is detachably connected to the distal bore of a hypodermic syringe. In a second embodiment, the combination cannula and collapsible needle cover is integrally connected to the distal bore of a syringe so as to form a one-piece, disposable syringe assembly.

The needle cover of the present invention comprises distally and proximally oriented pairs of needle cover segments, each of which segments being joined to an adjacent segment by means of an integral hinge around which said cover segments pivot. The needle cover is collapsible from an open, expanded configuration, at which the needle cannula is biased in an armed state for administering an injection, to a closed, generally planar configuration, at which the needle cannula is biased in a shielded state, to be completely surrounded and isolated by the cover. A pair of oppositely disposed, rotatable motion transferring arms is connected to the needle cover so that a health care worker may manually and selectively move the cover between the open and closed configurations.

A locking catch is connected to one of the needle cover segments and is adapted to move into respective engagement with adjacent cover segments to either releasably retain the needle cover in the open configuration with the cannula in the armed state or permanently lock the needle cover in the closed configuration with the cannula in the shielded state. Accordingly, the needle cannula may be safely disposed of after use within its collapsible cover to avoid subjecting the health care worker to an accidental needle strike and the spread of a contagious, and possibly life threatening, disease.

BRIEF DESCRIPTION OF THE DRAWINGS

FIG. 1 shows the collapsible needle cover according to a first embodiment of the invention detachably connected to the distal bore of a hypodermic syringe and moved to a closed, generally planar configuration for surrounding and shielding a disposable needle cannula;

FIG. 2 shows the collapsible needle cover of FIG. 1 in an open, generally expanded configuration to expose the needle cannula for the purpose of administering an injection of the fluid contents of the syringe;

FIGS. 3-5 illustrate the details for operating the needle cover of FIG. 1; and

DESCRIPTION OF THE PREFERRED EMBODIMENTS

Figure 6:
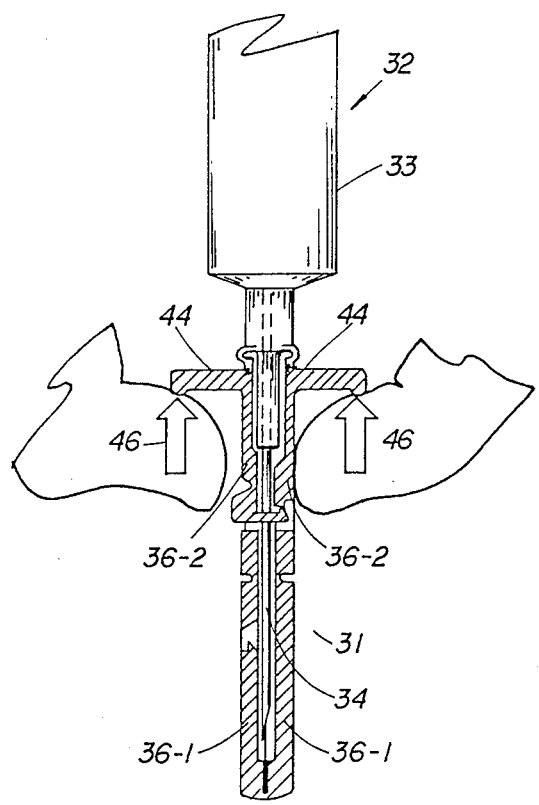
FIGS. 6 and 7 show the collapsible needle cover according to a second embodiment of the invention integrally connected to the distal bore of a hypodermic syringe to form a one-piece, disposable syringe assembly.

The collapsible needle cover according to a first embodiment of the present invention is best described while referring to FIGS. 1-5 of the drawings, where FIGS. 1 and 2 show the needle cover 1 detachably connected to the distal bore of the hollow cylinder 3 of a conventional hypodermic syringe (shown in phantom and represented by the reference numeral 2). The needle cover 1 is preferably, but not necessarily, fabricated from a radiation grade polypropylene material. FIG. 1 shows the needle cover 1 in a closed, generally planar configuration so as to completely surround, shield, and isolate a needle cannula 4 and thereby prevent an accidental needle strike and the spread of a contagious, and possibly life threatening disease. FIG. 2 shows the needle cover 1 in an open, expanded configuration to expose the cannula 4 and thereby permit said cannula to either communicate with a source of fluid (so that the syringe 2 may be infused with a medication, vitamin, or the like) or penetrate the skin of a patient (so that a piston 5 may be moved through cylinder 3 and an injection may be administered according to medically accepted techniques). As will soon be described, the collapsible needle cover 1 and needle cannula 4 are integrally connected to one another so as to be attached to or removed from the syringe 2 as a one piece, combination cannula/cover.

Referring to concurrently to FIGS. 1 and 2, the needle cover 1 is shown comprising distally and proximally oriented pairs of needle cover segments 6-1 and 6-2. Each needle cover segment 6-1 and 6-2 is joined to its adjacent segment by means of a respective, integral hinge 7 around which the cover pivots when moving between the closed and open configurations of FIGS. 1 and 2. A narrow orifice 8 is established through the hinge 7 at the intersection of the distally oriented cover segments 6-1, so as to receive the distal end of needle cannula 4 therethrough when the needle cover 1 is moved to the open, expanded configuration of FIG. 2.

The proximally oriented pair of needle cover segments 6-2 are connected to a needle support 10 by means of integral hinges 9. A conventional luer lock fitting 12 projects proximally from the needle support 10. In the assembled relationship of FIGS. 1 and 2, the luer lock fitting 12 of needle cover 1 is interconnected (i.e. rotated into engagement) with the distal bore of the syringe cylinder 3 whereby to detachably connect the needle cover 1 to the syringe 2. The needle support 10 is integrally connected (e.g. molded or thermally bonded) to the needle cannula 4 so as to support and retain the cannula in coaxial alignment with the luer lock fitting 12 and the cylinder 3 of syringe 2. Hence, the needle cover 1 and needle cannula 4 are packed and shipped to health care facilities as a single piece, combination cannula/cover. Moreover, and in the assembled relationship, the proximal end of cannula 4 communicates with the interior with the syringe cylinder 3 via the luer lock fitting 12, whereby the cylinder may be infused with fluid or fluid may be expulsed from the cylinder (with the needle cover 1 in the open, expanded configuration of FIG. 2).

A pair of motion transferring arms 14 projects outwardly and in opposite directions from respective proximally oriented needle cover segments 6-2. As will be explained when referring to FIG. 4 the motion transferring arms 14 may be manually rotated towards one another, whereby to cause the needle cover segments 6-1 and 6-2 to pivot around their respective hinges 8 and 9 and thereby cause needle cover 1 to move from the closed, substantially planar configuration of FIG. 1, to the open, expanded configuration of FIG. 2, such that needle cannula 4 is biased in an armed state from a shielded state.

A locking catch 16 extends from one of the proximally oriented cover segments 6-2. A first notch 18 is formed in the other of the proximally oriented cover segments 6-2. A second notch 20 is formed in the distally oriented cover segment 6-1 which lies immediately above and is contiguous with the proximally oriented cover segment 6-2 from which locking catch 16 extends. As will also be explained while referring to FIGS. 4 and 5, the locking catch 16 performs a dual function. In a first case, locking catch 16 is rotated through notch 20 to automatically and releasably retain needle cover 1 in the open, expanded configuration of FIGS. 2 and 4 and thereby permit the cylinder 3 of syringe 2 to be infused with fluid for the purpose of administering an injection. In a second case, locking catch 16 is rotated through notch 18 to automatically lock needle cover 1 in the closed, substantially planar configuration of FIGS. 1 and 5, whereby the needle cannula 4 is surrounded, shielded, and isolated to permit the cannula to be safely handled and discarded after use while avoiding an accidental needle strike.

The operation of the collapsible needle cover 1 is now describe while referring to FIGS. 3, 4, and 5 of the drawings. FIG. 3 shows the needle cover 1 immediately after its removal from a package in which said cover is transported to a health care facility. More particularly, a pre-sterilized needle cover 1 is packed in a substantially collapsed condition with the needle cover segments 6-1 and 6-2 thereof pivoted around their respective hinges 7 and 9 to the closed, generally planar configuration to surround needle cannula 4. However, to permit the cover 1 to be moved, by a health care worker, out of the collapsed condition, whereby needle cannula 4 may be biased in the armed state (of FIG. 4) from the shielded state (of FIG. 3) so that an injection may be administered, the locking catch 16 is located next to, but outside, the notch 18 in the adjacent proximally oriented cover segment 6-2. That is to say, the needle cover 1 is moved to but not locked in the closed, generally planar configuration.

The combination needle cover 1/needle cannula 4 is removed from its package with the cover in the collapsed configuration and the needle cannula 4 in the shielded state. The cover is then removably attached to the syringe 2 by rotating the luer lock fitting 12 of the cover into engagement with the distal bore of the syringe cylinder 3.

In FIG. 4, the needle cover 1 is moved out of the collapsed condition, so that needle cannula 4 can be biased in the armed state. More particularly, with the needle cover 1 attached to the cylinder 3 of syringe 2, the health care worker applies an axially and proximally directed force to each of the pair of motion transferring arms 14 (in the direction of the reference arrows 22 of FIG. 3). Accordingly, the arms 14 will rotate towards one another in a generally proximal direction, whereby to correspondingly cause needle cover segments 6-1 and 6-2 to pivot around their respective hinges 7 and 9 for movement to the open, expanded configuration of FIG. 4. During the relocation of needle cover 1 (in the direction of reference arrow 24), the locking catch 16, which extends from a proximally oriented cover segment 6-2 is advanced through the notch 20, whereby to be automatically snapped into engagement with its adjacent, contiguously disposed and distally oriented cover segment 6-1 in which the notch 20 is formed to releasably and reliably retain needle cover 1 in the open, expanded configuration. Moreover, the distal end of needle cannula 4 extends through the opening 8 in the hinge 7 between adjacent distally oriented cover segments 6-1, so that cannula 4 is held in the armed state at which syringe cylinder 3 is infused with fluid for subsequent injection through the skin of a patient.

After an injection is administered, and referring now to FIG. 5 of the drawings, the needle cover 1 is again collapsed whereby cover segments 6-1 and 6-2 are returned to the closed, generally planar configuration and needle cannula 4 is biased in the shielded state. More particularly, the health care worker detaches the locking catch 16 from (i.e. rotates locking catch 16 out of engagement with) the distally oriented needle cover segment 6-1, such that the catch is moved out of notch 20. With his thumb and index finger, the health care worker then applies equal and opposite, laterally directed forces (in the direction of the reference arrows 26) to the proximally oriented needle cover segment 6-2 to cause the segments 6-1 and 6-2 to pivot around their respective hinges 7 and 9 and thereby collapse needle cover 1 around needle cannula 4. The continued application of the laterally directed forces advances locking catch 16 through the notch 18 in the proximally oriented cover segment 6-2 in which said notch is formed.

Accordingly, locking catch 16 is automatically snapped into engagement with cover segment 6-2, whereby to permanently lock needle cover 1 in the closed, generally planar configuration with needle cannula 4 biased in the shielded state. Hence, the needle cover segments 6-1 and 6-2 surround, shield and isolate the cannula 4 so that the syringe 2 may be safely handled without subjecting the health care worker to an accidental needle strike and the spread contagious and possibly life-threatening disease. Since the locking catch 16 prevents the inadvertent return of the needle cover 1 to the open, expanded configuration (of FIG. 4), needle cover 1 may be detached from syringe cylinder 3. However, unlike many conventionally syringe assemblies, the needle cannula 4 need not be directly handled, cut, or otherwise destroyed after use, but may be conveniently and safely discarded in the shielded state of FIG. 5 within the collapsed needle cover 1.

Figure 7:
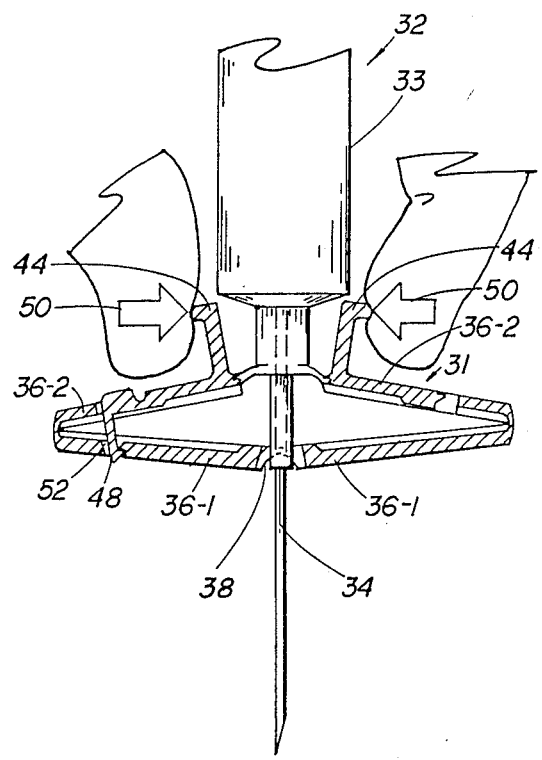

A collapsible needle cover 31 according to a second embodiment of the present invention is now described while referring to FIGS. 6 and 7 of the drawings. Like the needle cover 1 of FIGS. 1-5, the needle cover 31 of FIGS. 6 and 7 is integrally connected (e.g. molded or bonded) to a needle cannula 34. However, needle cover 31 is also integrally connected to the distal bore of a cylinder 33 from a syringe 32 so as to form a one-piece, disposable syringe assembly.

Needle cover 31 comprises distally and proximally oriented pairs of needle cover segments 36-1 and 36-2 which are hingedly interconnected with one another and adapted to pivot when cover 31 is moved between the closed and open configurations. That is, FIG. 6 shows the needle cover 36 in a closed, generally planar configuration with the needle cover segments 36-1 and 36-2 completely surrounding, shielding, and isolating the cannula 34 so as to prevent an accidental needle strike. FIG. 7 shows the needle cover 31 in the open, expanded configuration to expose the cannula 34 through an orifice 38 in the cover 31 and thereby permit the fluid contents of syringe 33 to be injected through the skin of a patient.

A pair of motion transferring arms 44 project outwardly and in opposite directions from respective proximally oriented needle cover segments 36-2. As previously disclosed when referring to FIGS. 4 and 5, axially and proximally directed forces may be manually applied to the motion transferring arms 44 (in the direction of the reference arrows 46 of FIG. 6) to cause said arms to rotate, whereby needle cover segments 36-1 and 36-2 are correspondingly pivoted around their respective hinges. Hence, the needle cover 31 is moved to the open, expanded configuration of FIG. 7 with needle cannula 34 biased in the armed state. The continued application of force to motion transferring arms 46 (in the direction of reference arrows 50) also causes a locking catch 48, which extends from a proximally oriented cover segment 36-2, to be advanced through a notch 52 and snapped into engagement with the adjacent and contiguously disposed distal cover segment 36-1 in which such notch is formed. Accordingly, the needle cover 31 is releasably retained in the open, expanded configuration of FIG. 7 so that an injection may be administered.

A description of the return of needle cover 31 to the closed, generally planar configuration of FIG. 6 with needle cannula 34 in the shielded state (suitable to permit the one-piece syringe 32 in the second embodiment to be safely discarded after use) is similar to that which was previously provided when referring to FIG. 5. Therefore, for purposes of brevity, this description will be omitted.

By virtue of the present invention, a reliable, safety enhancing needle cover is available which is integrally connected to a needle cannula and easily manipulated between open and closed configurations, whereby either an injection may be administered or the cannula may be completely surrounded, shielded, and isolated so as to be suitable for disposal after a single use without requiring the needle to be handled, cut or destroyed. Accordingly, a health care worker will not be subjected to the risk of an accidental needle strike and the spread of a contagious and life-threatening, disease.

It will be apparent that while the preferred embodiments of the invention have been shown and described various modifications may be made without departing from the true spirit and scope of the invention.

Having thus set forth a preferred embodiment of the invention what is claimed is:

1. A syringe including hollow cylinder means in which to receive a supply of fluid, a needle cannula communicating fluidically with said cylinder means so that the fluid can be expulsed therefrom, means for expulsing fluid from said cylinder means, and needle cover means, said needle cover means comprising:
   a needle cover that is collapsible from an open, expanded configuration, at which the cannula is exposed so that an injection may be administered, to a closed, generally planar configuration, at which the cannula is surrounded and shielded to avoid an accidental needle strike, said needle cover being split longitudinally and cross-sectionally to form proximal and distal pairs of cover segments, each cover segment having a proximal and distal end,
   first hinge means to interconnect the distal ends of said distal cover segments to one another,
   an opening through said first hinge means which is coaxial with the needle cannula,
   second hinge means to connect the proximal end of each distal cover segment to the distal end of the longitudinally adjacent proximal cover segment,
   third hinge means to interconnect the proximal end of each proximal cover segment with the needle cannula, and
   retaining means extending from a first cover segment and adapted to engage a second cover segment to releasably retain said needle cover in the open configuration or to engage a third cover segment to retain said needle cover in the closed configuration.

2. The syringe recited in claim 1, wherein said third hinge means further comprises means to connect the needle cannula to said needle cover to form an integral and non-detachable cannula and collapsible cover therefor.

3. The syringe recited in claim 1, further comprising means to connect the hollow cylinder means of the syringe to the needle cannula and said needle cover to form an integral and non-detachable assembly.

4. The syringe recited in claim 1, wherein said second hinge means are integrally formed between the longitudinally adjacent cover segments of said needle cover.

5. The syringe recited in claim 1, said needle cover means further comprising at least one motion transmitting arm extending outwardly from one of said needle cover segments and adapted to be transversely aligned with respect to the longitudinal axis of the cannula, the application of an axial force to said arm causing said proximal and distal pairs of cover segments to pivot relative to one another and said needle cover to move between said open and closed configurations.

6. The syring recited in claim 1, wherein said retaining means permanently locks said needle cover in the closed configuration with the needle cannula surrounded and shielded.

7. The syringe recited in claim 1, said needle cover means further comprising a notch formed through the second of said needle cover segments for receiving said retaining means therewithin and thereby retaining said needle cover in the open configuration.

8. The syringe recited in claim 1, said needle cover means further comprising a notch formed through the third of said needle cover segments for receiving said retaining means therewithin and thereby retaining said needle cover in the closed configuration.

9. The syringe recited in claim 1, wherein said retaining means includes a catch extending from said first needle cover segment to engage either said second needle cover segment which is longitudinally adjacent said first segment to releasably retain said needle cover in the open configuration or said third needle cover segment which is cross-sectionally opposite said first segment to retain said needle cover in the closed configuration.

10. The syringe recited in claim 1, further comprising means to connect said needle cover to the cylinder means of the syringe to form an integral and nondetachable syringe cylinder and needle cover assembly.

11. A syringe comprising a hollow cylinder in which to receive a supply of fluid, a needle cannula communicating fluidically with said cylinder so that fluid can be expulsed therefrom, means for expulsing fluid from said cylinder, and needle cover means being collapsible from an open, expanded configuration, at which the cannula is exposed so that an injection may be administered, to a closed, generally planar configuration, at which the cannula is surrounded and shielded to avoid an accidental needle strike, said needle cover means including:

first and second sets of cover segments, each set of cover segments having a first and a second end, the segments forming said first set of cover segments extending longitudinally adjacent one another along one side of the needle cannula, and the segments forming said second set of cover segments extending along the opposite side of the needle cannula in opposing alignment with said first set of cover segments;

first hinge means located between adjacent cover segments of said first and second sets, such that said needle cover means is collapsible at said hinge means from the open configuration to the closed, generally planar configuration at which the cannula is surrounded and shielded;

second hinge means to connect respective first ends of said first and second sets of cover segments together;

third hinge means to interconnect respective second ends of said first and second sets of cover segments with the needle cannula;

an opening through said second hinge means in coaxial alignment with the needle cannula; and catch means extending from a first of said cover segments and adapted to engage a second of said cover segments to releasably retain said needle cover means in the open configuration or to engage a third of said cover segments to retain said needle cover means in the closed configuration.

12. The syringe recited in claim 11, wherein said first and second cover segments are from said first and second sets, respectively, of needle cover segments.

13. The syringe recited in claim 11, wherein said first and third cover segments are from said first set of cover segments.

* * * * *